United States Patent
Ahtchi-Ali

(10) Patent No.: US 10,772,345 B2
(45) Date of Patent: Sep. 15, 2020

(54) BEVERAGE NANOEMULSTIONS PRODUCED BY HIGH SHEAR PROCESSING

(71) Applicant: PepsiCo, Inc., Purchase, NY (US)

(72) Inventor: Badreddine Ahtchi-Ali, Montebello, NY (US)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 16/033,584

(22) Filed: Jul. 12, 2018

(65) Prior Publication Data

US 2018/0317525 A1 Nov. 8, 2018

Related U.S. Application Data

(62) Division of application No. 14/952,159, filed on Nov. 25, 2015, now abandoned.

(51) Int. Cl.

| A23L 2/56 | (2006.01) |
| A61K 47/12 | (2006.01) |
| A61K 47/36 | (2006.01) |
| A61K 47/44 | (2017.01) |
| A23L 27/00 | (2016.01) |
| A23L 2/52 | (2006.01) |
| A23L 2/62 | (2006.01) |
| A61K 9/00 | (2006.01) |
| A61K 9/107 | (2006.01) |
| A61K 36/889 | (2006.01) |

(52) U.S. Cl.
CPC .............. *A23L 2/56* (2013.01); *A23L 2/52* (2013.01); *A23L 2/62* (2013.01); *A23L 27/80* (2016.08); *A61K 9/0095* (2013.01); *A61K 9/1075* (2013.01); *A61K 36/889* (2013.01); *A61K 47/12* (2013.01); *A61K 47/36* (2013.01); *A61K 47/44* (2013.01); *A23V 2002/00* (2013.01)

(58) Field of Classification Search
CPC .. A61K 9/1075; A61K 9/0095; A61K 36/889; A61K 47/12; A61K 47/44; A23L 2/56; A23L 2/52; A23L 2/62; A23L 27/80
See application file for complete search history.

(56) References Cited

U.S. PATENT DOCUMENTS

| 4,705,691 A * | 11/1987 | Kupper ............... A23L 2/62 426/590 |
| 5,616,358 A | 4/1997 | Taylor et al. |
| 6,576,285 B1 | 6/2003 | Bader et al. |
| 7,601,380 B2 | 10/2009 | Fang et al. |
| 8,318,233 B2 | 11/2012 | Tran et al. |
| 8,435,581 B2 | 5/2013 | Fang et al. |
| 2002/0110533 A1 | 8/2002 | Huff et al. |
| 2003/0215470 A1 | 11/2003 | Wilmott et al. |
| 2004/0142087 A1 | 7/2004 | Lerchenfeld et al. |
| 2005/0089621 A1 | 4/2005 | Aquino et al. |
| 2005/0208009 A1* | 9/2005 | Bonnardel ............ A61K 8/732 424/70.13 |
| 2006/0159633 A1 | 7/2006 | Wajda |
| 2007/0110874 A1* | 5/2007 | Fang .................... A23F 3/163 426/590 |
| 2008/0274195 A1 | 11/2008 | Nicolosi et al. |
| 2010/0305218 A1 | 12/2010 | Wooster et al. |
| 2011/0236558 A1* | 9/2011 | Tran .................... A23L 29/10 426/602 |
| 2011/0268847 A1* | 11/2011 | Yang .................... A23L 2/02 426/74 |
| 2012/0135125 A1 | 5/2012 | Muschiolik et al. |

FOREIGN PATENT DOCUMENTS

| EP | 2025250 A1 | 2/2009 |
| GB | 1 537 160 A | 12/1978 |
| RU | 2358715 C2 | 1/2006 |
| WO | WO 99/38389 A2 | 8/1999 |

OTHER PUBLICATIONS

Mason T.G., Wilking, J.N., Meleson, K., Chang, C.X., Graves, S.M., Nanoemulsions: formation, structure, and physical properties, Journal of Physics: Condensed Matter, vol. 18, No. 41, pp. 635-666, Sep. 29, 2006. (Year: 2006).*
Industrial Mixers, Homogenizer Information, [on line] Aug. 25, 2015, retrieved Aug. 1, 2019. Retrieved from the Internet: URL:<http://web.archive.org/web/20150825061148/https://www.industrialmixers.com/homogenizer/>.*
Silverson Machines, Inc., Manufacture of Cloud Emulsions for Soft Drinks, Application Report, Silverson High Shear Mixers/Emulsifiers, Issue No. 44FA2, accessed at http://www.silverson.com/images/uploads/documents/FCloudEmulsions.pdf, accessed on May 12, 2017, 4 pages.
International Search Report and Written Opinion for International Application No. PCT/US16/62768, ISA/US, Commissioner for Patents, United States, dated Feb. 3, 2017, 9 pages.
"Gaulin Homogenizer," Dairy Engineering, accessed at http://gaulinhomogenizer.com/, accessed on Dec. 13, 2017, 6 pages.

* cited by examiner

*Primary Examiner* — Viren A Thakur
*Assistant Examiner* — Chaim A Smith
(74) *Attorney, Agent, or Firm* — Sterne, Kessler, Goldstein & Fox P.L.L.C.

(57) ABSTRACT

The present disclosure relates beverage nanoemulsions and methods for making such beverage nanoemulsions. More particularly, the present disclosure relates to methods for making beverage nanoemulsions using high shear processing.

13 Claims, 11 Drawing Sheets

BEVERAGE NANOEMULSTIONS PRODUCED BY HIGH SHEAR PROCESSING

FIELD AND BACKGROUND OF THE INVENTION

The present disclosure relates beverage nanoemulsions md methods for making such beverage nanoemulsions. More particularly, the present disclosure relates to methods for making beverage nanoemulsions using high shear processing.

Beverage nanoemulsions are typically oil-in-water emulsions with particle sizes below 1 micron, i.e., $d_{95}$<1 micron. These nanoemulsions comprise flavour or cloud oils, emulsifiers, water, and optionally preservatives. Levels of oil range between 6 and 10 wt % in the emulsion concentrate. Also a weight ratio of emulsifier to oil greater than 1:1 is used in combination with a target oil particle size of $d_{95}$<1 micron to ensure physical stability in the beverage nanoemulsion and in the final beverage product.

The current manufacturing process for making these beverage nanoemulsions consists of two steps: (1) dispersing/dissolving the emulsifier in water, and then adding the cloud or flavor oil to form an emulsion premix in a mixing tank; emulsion particle sizes are typically $d_{95}$>2 microns, needing further size reduction; (2) pumping the emulsion pre-mix formed in step (1) to a high pressure homogenizer (pressure between 3000 and 5000 psi) to break down the oil droplets to the target particle sizes ($d_{95}$<1 micron). This two-step process is time consuming and energy intensive. Additionally, concentrated, viscous emulsions with less water cannot be produced with the current process. The high pressure homogenizers cannot handle concentrated, viscous emulsions due to their inherent design (small orifice of the homogenizer get clogged). Therefore, there is a need for alternative methods for making concentrated beverage nanoemulsions to address the limitations of the abovementioned process.

BRIEF SUMMARY OF THE INVENTION

This Summary is provided to introduce a selection of concepts in a simplified form that are further described below in the Detailed Description. This Summary is not intended to identify key or essential features of the invention.

In one aspect, a method is provided for producing both concentrated and dilute nanoemulsions, eliminating the homogenization step, thereby reducing the batch cycle time by up to 50%. This process comprises producing highly concentrated oil-in-water nanoemulsions using high shear mixing. Nanoemulsion particle sizes, meeting the target sizes required for beverage stability, have been achieved via high shear mixing without the need to homogenize when high oil levels/viscosities are used. Concentrated emulsions can be delivered as is or diluted to desired oil levels and viscosities.

In one aspect, the present disclosure provides a method for preparing a beverage nanoemulsion, comprising the steps of:
   (a) providing a mixture comprising an oil, an emulsifies water, and optionally a preservative; and
   (b) mixing the mixture with a high shear mixer to obtain the nanoemulsion, wherein the mixture has a viscosity of 2800 cp at 10 s$^{-1}$ to 50,000 cp at 10 s$^{-1}$ during at least a part of the mixing; and wherein the nanoemulsions has a particle size of $d_{95}$ from 0.05 micron to 1 micron. In one aspect, the mixture contains 12 wt % to 40 wt % of the oil.

In one aspect, the present disclosure provides a beverage nanoemulsions comprising:
   (a) an oil in an amount from 12 wt % to 40 wt%;
   (b) an emulsifier in an amount from 1 wt % to 30 wt %;
   (c) optionally a preservative; and
   (d) water;
wherein, the nanoemulsion has a particle size of $d_{95}$ from 0.05 micron to 1 micron and a viscosity of 2800 cp at 10 s$^{-1}$ to 50,000 cp at 10 s$^{-1}$.

The wt % amounts in the specification refer to the amounts of an active ingredient in the final beverage nanoemulsion.

BRIEF DESCRIPTION OF THE DRAWINGS

Some embodiments are illustrated by way of example, and not by way of limitation, in the figures of the accompanying drawings.

DETAILED DESCRIPTION OF THE INVENTION

Definitions

Figure 1:
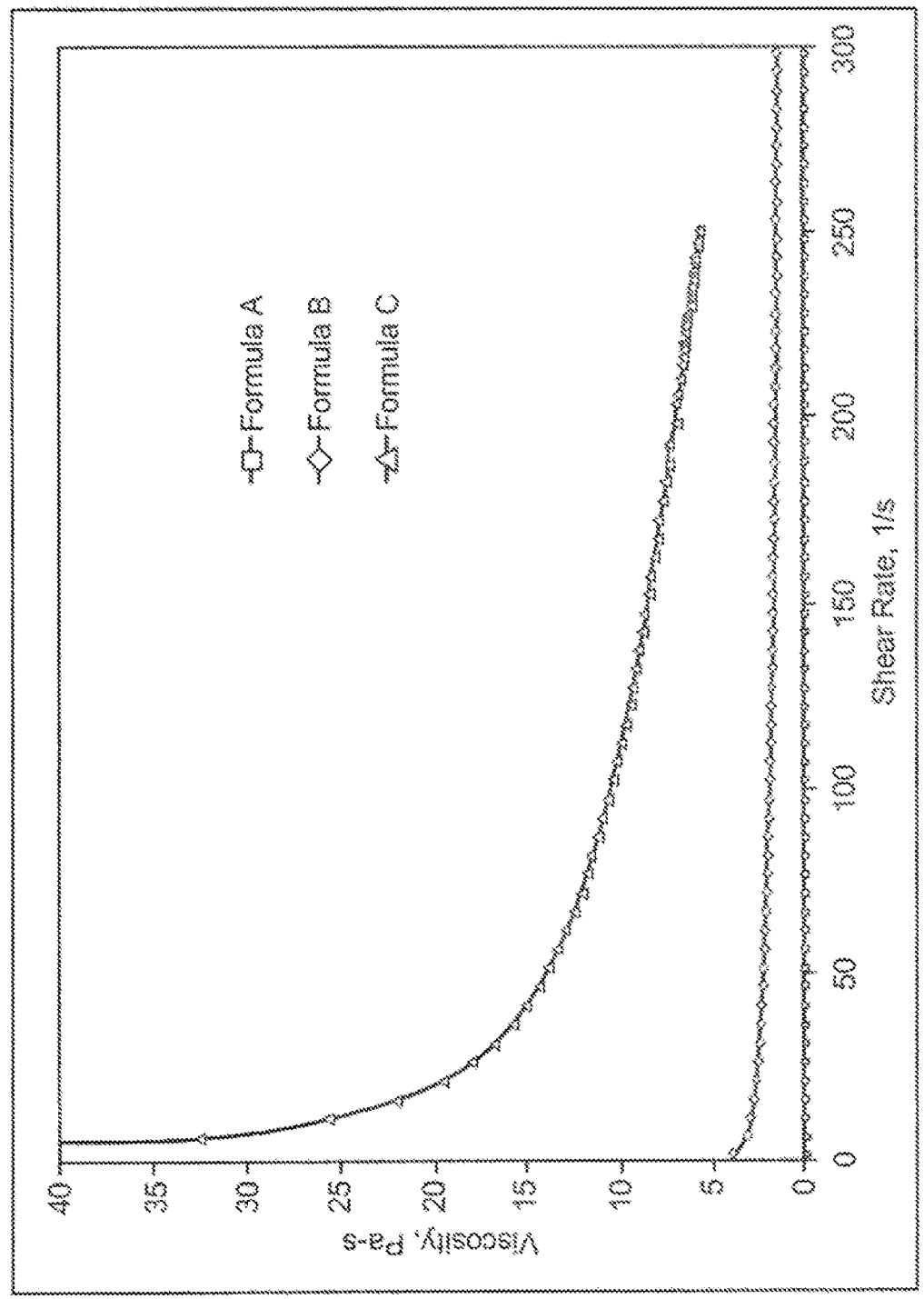
FIG. 1 shows viscosities of unprocessed formulas A-C.

Unless specifically stated or obvious from context, as used herein, the numeric values disclosed herein are understood as within a range of normal tolerance in the art, for example, within 10% of the stated value. The wt % amounts in the specification refer to the amounts of an active ingredient in the final beverage nanoemulsion.

Open terms such as "include," "including," "contain," "containing" and the like mean "comprising." These open-ended transitional phrases are used to introduce an open ended list of elements, method steps or the like that does not exclude additional, unrecited elements or method steps.

The transitional phrase "consisting of" and variations thereof excludes any element, step, or ingredient not recited, except for impurities ordinarily associated therewith.

The transitional phrase "consists essentially of," or variations such as "consist essentially of" or "consisting essentially of," excludes any element, step, or ingredient not recited except for those that do not materially change the basic or novel properties of the specified method, structure or composition.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The terms "invention" or "present disclosure" as used herein are non-limiting terms and are not intended to refer to any single embodiment of the particular invention but encompass all possible embodiments as described in the application.

Method of Preparing Beverage Nanoemulsions

In one aspect, the present disclosure provides a method for preparing a beverage nanoemulsion, comprising the steps of:

(a) providing a mixture comprising an oil, an emulsifier, water, and optionally a preservative; and (b) mixing the mixture with a high shear mixer to obtain the nanoemulsion, wherein the mixture has a viscosity of 2800 cp at $10 \, s^{-1}$ to 50,000 cp at $10 \, s^{-1}$ during at least a part of the mixing; and wherein the nanoemulsion has a particle size of $d_{95}$ from 0.05 micron to 1 micron.

In one aspect, the mixture contains 12 wt % to 40 wt % of the oil.

In one aspect, the method for preparing a beverage nanoemulsion further comprises adding water to the nanoemulsion to obtain a diluted nanoemulsion, wherein the diluted nanoemulsion contains 6 wt % to 10 wt % of the oil, and wherein the diluted nanoemulsion has a particle size of $d_{95}$ from 0.05 micron to 1 micron.

In one aspect, the present disclosure provides a beverage nanoemulsion comprising:

(a) an oil in an amount from 12 wt % to 40 wt %;
(b) an emulsifier in an amount from 1 wt % to 30 wt %;
(c) optionally a preservative; and
(d) water;

wherein the nanoemulsion has a particle size of $d_{95}$ from 0.05 micron to 1 micron and a viscosity of 2800 cp at $10 \, s^{-1}$ to 50,000 cp at $10 \, s^{-1}$.

In some embodiments, the oil used in the present disclosure is a hydrophobic clouding agent. The hydrophobic clouding agent can be selected from sterol esters, stanol esters, and combinations thereof.

Sterol and stanol esters, in addition to providing the cloudiness, have been shown to provide health benefits such as reducing low-density lipoprotein (LDL) cholesterol levels in humans when consumed in amounts of about 1.3 grams per day on a regular basis. The sterol and stanol esters are the esterified forms of the free sterols and stanols respectively. Stanols are the saturated or hydrogenated form of the sterols or plant sterols.

Plant sterols can be derived from vegetable oils or tall oil. Common sources of sterols from vegetable oils include, but are not limited to, coconut oil, corn oil, cotton oil, olive oil, palm oil, peanut oil, rapeseed oil, canola oil, safflower oil, linseed oil, cotton seed oil, soybean oil, sunflower oil, walnut oil, and avocado oil. Additionally, sterols can be derived from tall oil. Tall oil can be obtained from the wood of coniferous plants.

Stanols in the free and esterified forms and esterified sterols are not as readily available from natural sources as the free sterols. Thus, the free sterols must be hydrogenated to produce free stanols; and the free sterols and stanols must be esterified to produce sterol esters and stanol esters. Suitable sterols and stanols in esterified forms are commercially available from Raisio Benecol and McNeil Nutritionals, under the trade name Benecol®, from Archer Daniels Midland under the trade name CardioAid®, from Cognis under the trade name VegaPure®, from MultiBene Group under the trade name MultiBene® and others as known in the art.

In some embodiments, the oil includes, but is not limited to, flavorless oils, flavor oils, and combinations thereof.

Non-limiting examples of flavorless oils include medium chain triglycerides, vegetable oils, grapeseed oil, and the like, as is known to those skilled in the art. Non-limiting examples of suitable vegetable oils include soybeans, palm, rapeseed, sunflower seed, peanut, cotton seed, olive, avocado, coconut, safflower, other vegetable oils as is known to those skilled in the art, and combinations thereof. In one embodiment, the oil is coconut oil.

Non-limiting examples of flavor oils include citrus oils, cola oils, essential oils, and the like, as is known in the art. Non-limiting examples of essential oils include almond, grapefruit, cinnamon, lemon, lime, orange, peppermint, tangerine, other essential oils as is known to those skilled in the art, and combinations thereof.

In some embodiments, the oil is present in the beverage nanoemulsions in an amount from 10 wt % to 50 wt %. In some embodiments, the oil is present in the beverage nanoemulsion in an amount from 12 wt % to 40 wt %, from 12 wt % to 35 wt %, from 12 wt % to 30 wt %, from 12 wt % to 25 wt %, from 12 wt % to 20 wt %, from 16 wt % to 40 wt %, from 16 wt % to 35 wt %, from 16 wt % to 30 wt %, from 16 wt % to 25 wt %, from 16 wt % to 20 wt %, from 20 wt % to 40 wt %, from 20 wt % to 35 wt %, from 20 wt % to 30 wt %, from 20 wt % to 25 wt %, from 25 wt % to 40 wt %, from 25 wt % to 35 wt %, from 25 wt % to 30 wt %, from 30 wt % to 40 wt %, from 30 wt % to 35 wt %, and from 35 wt % to 40 wt %. In some embodiments, the oil is present in the beverage nanoemulsion in an amount from 14 wt % to 30 wt %, from 14 wt % to 28 wt %, from 14 wt % to 26 wt %, from 14 wt % to 24 wt %, from 14 wt % to 22 wt %, and from 14 wt % to 20 wt %. In some embodiments, the oil is present in the beverage nanoemulsions in an amount of 16 wt % and 20 wt %. The desired amount of oil may depend on the viscosity of the nanoemulsion.

In some embodiments, beverage nanoemulsions with a higher percentage of an oil can be diluted with water to obtain beverage nanoemulsions with a lower percentage of the oil.

In some embodiments, the emulsifier used in the present disclosure includes, but is not limited to, gum arabic, modified starch, pectin, xanthan gum, guar gum, propylene glycol alginate, monoglyceride, diglyceride, dioctyl sulfosuccinate sodium (DOSS), polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), sorbitan monolaurate (Span® 20), sorbitan monopalmitate (Span® 40), betaine, other emulsifiers as is known to those skilled in the art, and combinations thereof. Preferably, the emulsifier is selected from the group consisting of gum arabic, modified starch, pectin, xanthan gum, guar gum, propylene glycol alginate, and combinations thereof. In one embodiment, the emulsifier is modified starch.

In some embodiments, the emulsifier is present in the beverage nanoemulsions in an amount from 1 wt % to 40 wt %. In some embodiments, the emulsifier is present in the beverage nanoemulsion in an amount from 1 wt % to 30 wt %, from 1 wt % to 25 wt %, from 1 wt % to 20 wt %, from 1 wt % to 15 wt %, from 5 wt % to 30 wt %, from 5 wt % to 25 wt %, from 5 wt % to 20 wt %, from 5 wt % to 15 wt %, from 10 wt % to 30 wt %, from 10 wt % to 25 wt %, from 10 wt % to 20 wt %, from 10 wt % to 15 wt %, from 15 wt % to 30 wt %, from 15 wt % to 25 wt %, from 15 wt % to 20 wt %, from 20 wt % to 30 wt %, and from 20 wt % to 25 wt %. In some embodiments, the emulsifier is present in the beverage nanoemulsions in an amount of 14 wt %, 16 wt %, 18 wt %, 20 wt %, 22 wt %, 24 wt %, 26 wt %, 28 wt %, and 30 wt %. The desired amount of emulsifier may depend on the amount of oil present and the type of emulsifier, and should be sufficient to make a stable nanoemulsion.

In some embodiments, the beverage nanoemulsions further comprises a preservative. Non-limiting examples of preservatives include citric acid, sorbic acid, benzoic acid, alkali metal salts thereof, and any mixtures thereof.

High shear mixing can be performed by any suitable mixer known to those skilled in the art. Non-limiting examples of suitable mixers include turbine agitators, static mixers, and other high shear mixers known to those skilled in the art. Turbine agitators are commercially available from Scott Turbon® Mixer, Inc., Adelanto, Calif., and others as is known in the art. Static mixers, sometimes known in the art as motionless mixers or in-line mixers, come in various sizes and geometries and are commercially available from Chemineer Inc., Dayton, Ohio, Sulzer Chemtech Ltd., a member of the Sulzer Corp., Winterhur, Switzerland, Charles Ross & Son Co., Hauppauge, N.Y., and others as is known in the art.

High shear mixers have two parallel surfaces placed closely together. The material to be mixed is between the surfaces. The shear rate is the relative velocity of the surfaces divided by the distance between the surfaces. The surfaces may have a variety of configurations, such as parallel plates or annular cylindrical surfaces. Any shear mixer known to the art that is capable of achieving the shear rate described herein may be used. The shear rate in rotor stator mixers, $\gamma$ ($s^{-1}$), is the ratio between the rotor tip speed, $V_{tip}$ (m/s), and the gap between the stator and rotor, g (m). Rotor tip speed, $V_{tip}=\pi*D*n$, where D is the rotor diameter, (m), and n is the rotational speed in revolutions per second (n is defined as RPM/60).

In some embodiments, the mixture comprising the oil and the emulsifier is mixed at a shear rate of 20,000 $s^{-1}$ to 300,000 $s^{-1}$. In some embodiment, the mixture comprising the oil and the emulsifier is mixed at a shear rate of at least 20,000 $s^{-1}$, at least 30,000 $s^{-1}$, at least 50,000 $s^{-1}$, at least 100,000 $s^{-1}$, at least 150,000 $s^{-1}$, at least 200,000 $s^{-1}$, at least 250,000 $s^{-1}$, and at least 300,000 $s^{-1}$. In some embodiments, the mixture comprising the oil and the emulsifier is mixed at a shear rate from 20,000 $s^{-1}$ to 300,000 $s^{-1}$, 30,000 $s^{-1}$ to 300,000 $s^{-1}$, from 50,000 $s^{-1}$ to 300,000 $s^{-1}$, from 100,000 $s^{-1}$ to 300,000 $s^{-1}$, from 150,000 $s^{-1}$ to 300,000 $s^{-1}$, from 200,000 $s^{-1}$ to 300,000 $s^{-1}$, from 250,000 $s^{-1}$ to 300,000 $s^{-1}$, from 20,000 $s^{-1}$ to 250,000 $s^{-1}$, from 20,000 $s^{-1}$ to 200,000 $s^{-1}$, from 20,000 $s^{-1}$ to 200,000 $s^{-1}$, from 20,000 $s^{-1}$ to 150,000 $s^{-1}$, from 20,000 $s^{-1}$ to 100,000 $s^{-1}$, from 20,000 $s^{-1}$ to 50,000 $s^{-1}$, and from 20,000 $s^{-1}$ to 30,000 $s^{-1}$.

The viscosities of the mixture comprising an oil, an emulsifier, and water can be measured by using an Anton Paar RheoQC Rheometer. Concentric cylinder (CC27) measuring cup and corresponding Spindle are used to measure viscosity versus shear rate profiles for these emulsions. Different types of equipment used to measure viscosity can result in different measured values for the same sample. The values discussed herein were measured on an Anton Paar RheoQC Rheometer, and should be compared to values measured on the same equipment. In some embodiments, the mixture has a viscosity of 2800 centipoise (cp) at 10 $s^{-1}$ to 50,000 cp at 10 $s^{-1}$ during at least a part of the high shear mixing. In some embodiments, the mixture has a viscosity of from 3000 cp at 10 $s^{-1}$ to 50,000 cp at 10 $s^{-1}$, from 5000 cp at 10 $s^{-1}$ to 50,000 cp at 10 $s^{-1}$, from 10,000 cp at 10 $s^{-1}$ to 50,000 cp at 10 $s^{-1}$, from 20,000 cp at 10 $s^{-1}$ to 50,000 cp at 10 $s^{-1}$, from 30,000 cp at 10 $s^{-1}$ to 50,000 cp at 10 $s^{-1}$, and from 40,000 cp at 10 $s^{-1}$ to 50,000 cp at 10 $s^{-1}$. In some embodiments, the mixture has a viscosity of from 2800 cp at 10 $s^{-1}$ to 40,000 cp at 10 $s^{-1}$, from 2800 cp at 10 $s^{-1}$ to 30,000 cp at 10 $s^{-1}$, from 2800 cp at 10 $s^{-1}$ to 20,000 cp at 10 $s^{-1}$, from 2800 cp at 10 $s^{-1}$ to 10,000 cp at 10 $s^{-1}$, from 2800 cp at 10 $s^{-1}$ to 5000 cp at 10 $s^{-1}$, from 2800 cp at 10 $s^{-1}$ to 4000 cp at 10 $s^{-1}$, and from 2800 cp at 10 $s^{-1}$ to 3000 cp at 10 $s^{-1}$.

The particle size of the beverage nanoemulsions can be measured by using a laser diffraction particle size analyzer capable of measuring particle sizes ranging between 30 nm and 3000μ). Horiba LA-950 model was used to measure the particle size distributions of the nanoemulsions. Unless otherwise stated, the particle size or particle diameter in the present disclosure refers to $d_{95}$ of the particles. In some embodiments, the beverage nanoemulsion has a particle size of $d_{95}$ from 0.05 micron to 1 micron. In some embodiments, the beverage nanoemulsion has a particle size of $d_{95}$ of 0.05 micron, 0.1 micron, 0.2 micron, 0.3 micron, 0.4 micron, 0.5 micron, 0.6 micron, 0.7 micron, 0.8 micron, and 0.9 micron. In some embodiments, the beverage nanoemulsion has a particle of $d_{95}$ from 0.1 micron to 1 micron, from 0.2 micron to 1 micron, from 0.3 micron to 1 micron, from 0.4 micron to 1 micron, from 0.5 micron to 1 micron, from 0.6 micron to 1 micron, from 0.7 micron to 1 micron, from 0.8 micron to 1 micron, and from 0.9 micron to 1 micron. In some embodiments, the beverage nanoemulsion has a particle size of $d_{95}$ from 0.2 micron to 0.8 micron, from 0.3 micron to 0.6 micron, and 0.4 micron to 0.5 micron.

Those skilled in the art will appreciate that the beverage nanoemulsions according to the present invention can be incorporated into a beverage at any suitable stage of the beverage manufacturing process.

The examples which follow are intended as an illustration of certain preferred embodiments of the invention, and no limitation of the invention is implied.

EXAMPLES

Concentrated beverage nanoemulsions can be produced by using a mixing tank equipped with internal or external high shear rotor stator mixer. Disclosed here is a method for producing concentrated nanoemulsions (12 wt % to 40 wt % oil) using high shear mixing. Also disclosed here is a method for producing dilute nanoemulsions (6 wt %-10 wt % oil) by diluting the concentrated nanoemulsions with water to desired levels. The disclosed methods will reduce batch cycle time and eliminate tire need for high pressure homogenization.

Example 1: Formulas A-C

Three types of formulas were used as shown Table 1. Formula A is the standard formulation with 10 wt % coconut oil. Formulas B and C were more concentrated than formula A, providing 38% and 50% volume reduction, respectively. Formulas A-C were obtained by mixing the specified amount of coconut oil, modified food starch, sodium benzoate, citric acid, and water.

TABLE 1

Compositions of three formulas used for preparing beverage nanoemulsions.

|  | Formula A (wt %) | Formula B (wt %) | Formula C (wt %) |
|---|---|---|---|
| Coconut oil | 10 | 16.1 | 20 |
| Modified food starch (EmCap ®) | 14 | 22.5 | 28 |
| Sodium benzoate | 0.1 | 0.16 | 0.2 |
| Citric acid | 0.15 | 0.24 | 0.3 |
| Treated water | 75.75 | 61 | 51.5 |

Formulas A-C have different viscosities. Formulas B and C were more viscous than formula A (FIG. 1 and Table 2). Formula C cannot be processed through the high pressure homogenizer due to its high viscosity. Anton Paar RheoQC Rheometer with concentric cylinder (CC27) measuring Cup and corresponding Spindle was used to measure viscosity versus shear rate profiles of formula A-C.

TABLE 2

Viscosities of three formulas after the ingredients being mixed without further processing.

|  | 10 $s^{-1}$ | 100 $s^{-1}$ | 250 $s^{-1}$ |
|---|---|---|---|
| Formula A | 35.6 | 46.4 | 47 |
| Formula B | 2980 | 1950 | 1570 |
| Formula C | 25600 | 10300 | 5650 |

Example 2: High Shear Processing of Pre-Emulsified Mixture

Formulas A-C were pre-emulsified in a pre-mixing vessel equipped with a turbine agitator operated at 150 RPM, at 25° C. for 30 minutes.

Figure 2:
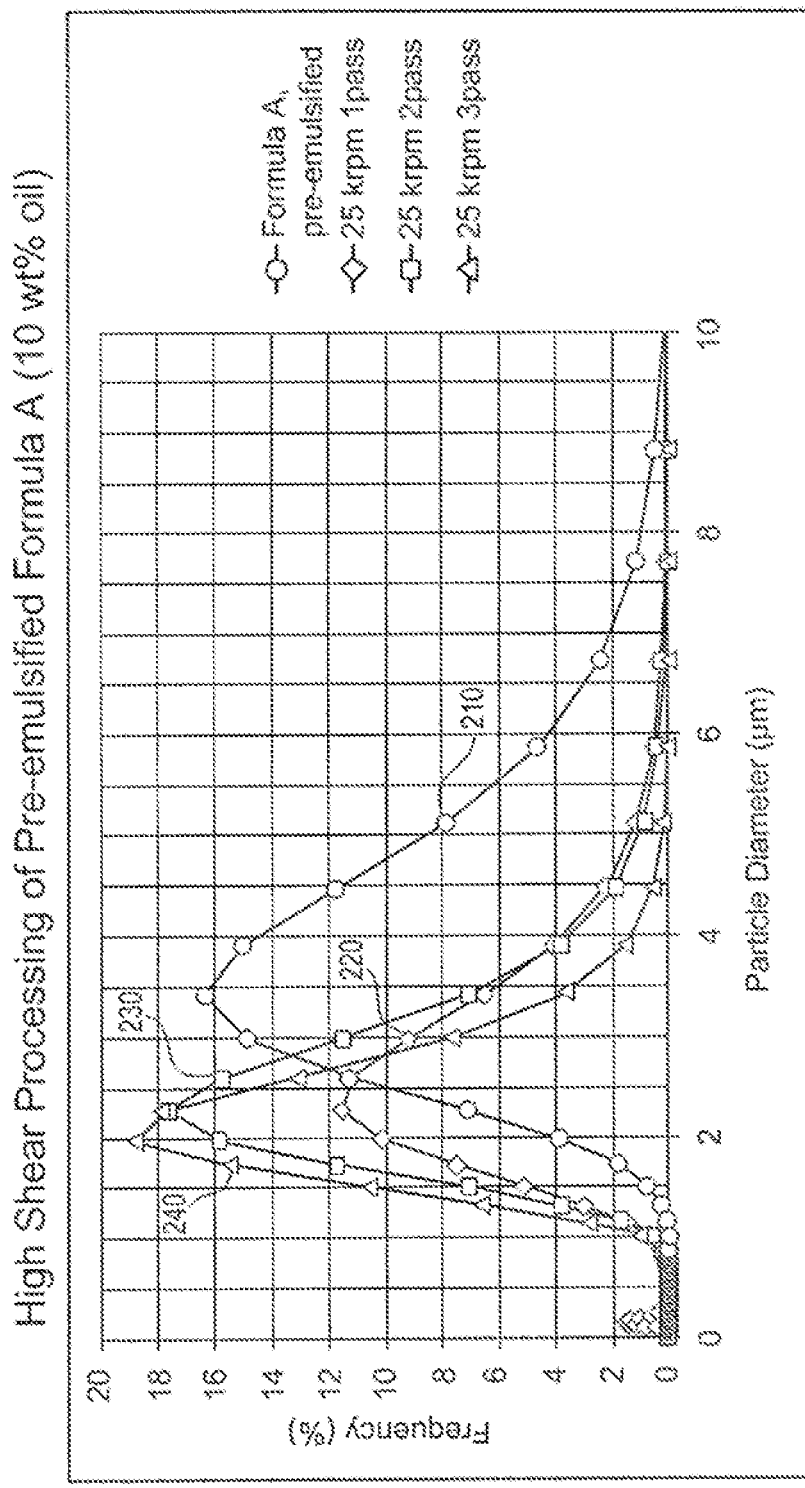
FIG. 2 shows particle sizes of the emulsions obtained from high shear processing of pre-emulsified formula A, and the particle size of the pre-emulsified formula A.
Figure 3:
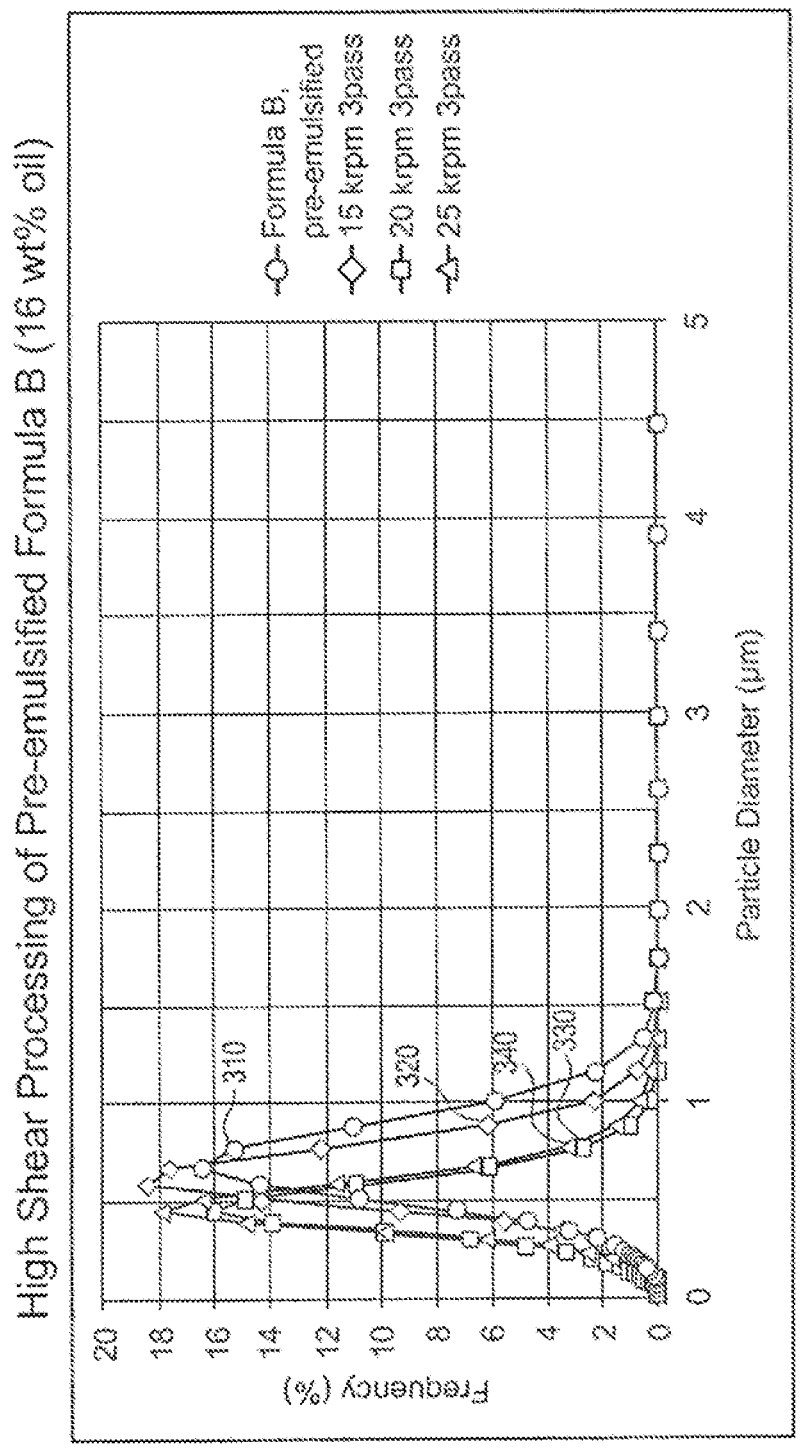
FIG. 3 shows particle sizes of the emulsions obtained from high shear processing of pre-emulsified formula B, and the particle size of the pre-emulsified formula B.
Figure 4:
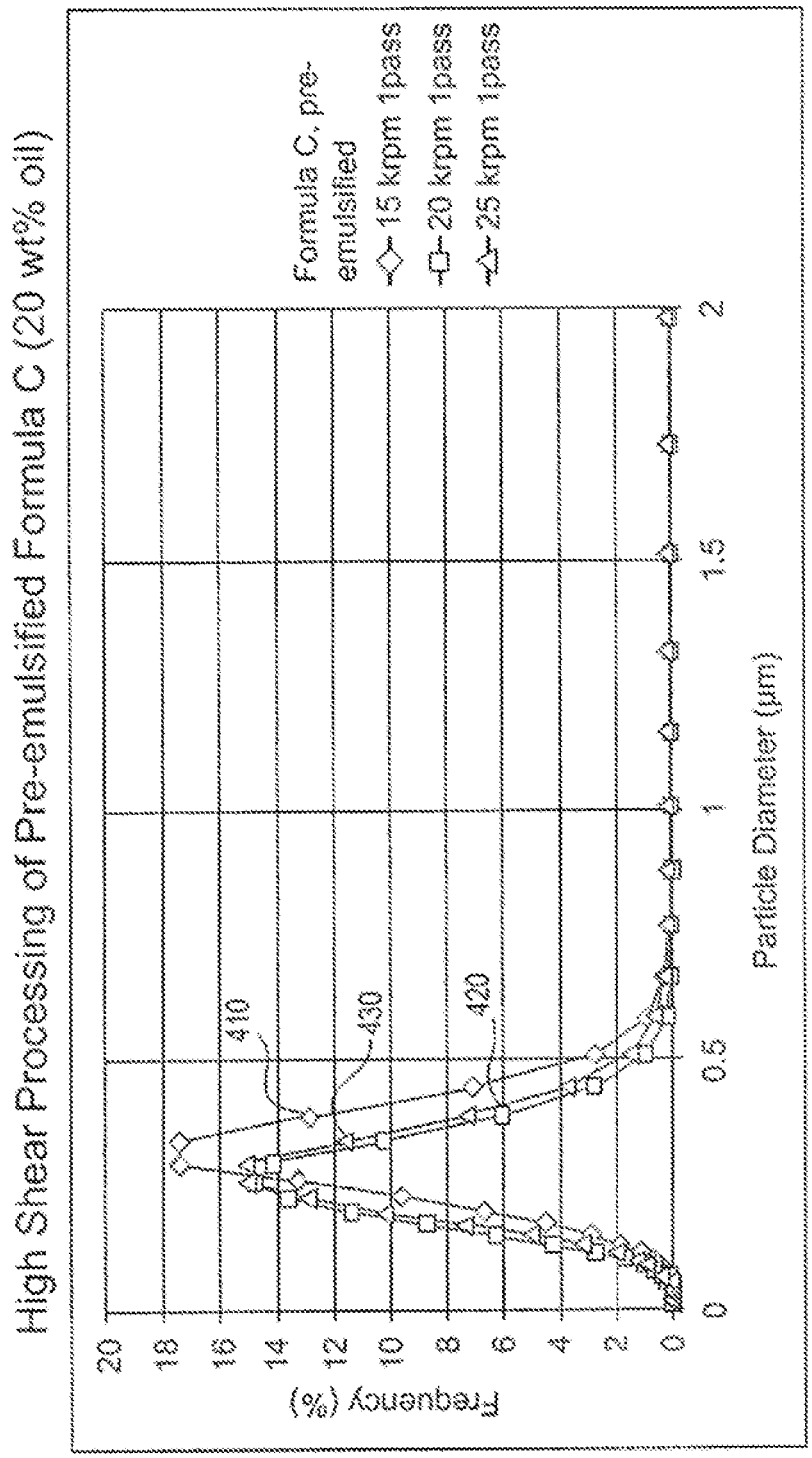
FIG. 4 shows particle sizes of the emulsions obtained from high shear processing of pre-emulsified formula C.

The pre-emulsified mixtures were then processed in a high shear rotor stator mixer, and the results were shown in FIGS. 2-4. The shear range for the rotor stator mixer case is as follows: 300000 $s^{-1}$ for 25 k RPM, 240,000 $s^{-1}$ for 20 k RPM and 180,000 $s^{-1}$ for 15 k RPM.

Pre-emulsified formula A (10 wt % oil) had $d_{95}$ of greater than 7 µm, as illustrated by curve 210 in FIG. 2. Pre-emulsified formula A was processed with a high shear rotor stator mixer with shear rates of up to 300,000 $s^{-1}$ (25 k RPM) for 5 minutes, in a recirculation mode for up to 3 passes. Curves 220, 230, and 240 in FIG. 2 show that the particle size ($d_{95}$) of the resultant emulsions after one, two, and three passes is 5.0, 4.1, and 3.1 µm, respectively.

Pre-emulsified formula B (16 wt % oil) had a particle size ($d_{95}$) of greater than 1 µm, as illustrated by curve 310 in FIG. 3. The emulsions obtained from three passes of high shear processing with 15 k, 20 k, and 25 k RPM had a particle size ($d_{95}$) of 0.83, 0.65, and 0.69 µm, respectively, as indicated by curves 320, 330, and 340 in FIG. 3.

For pre-emulsified formula C (20 wt % oil), it only requires one pass of high shear processing with a shear rate of 180,000-300,000 $s^{-1}$ to produce emulsions with a particle size ($d_{95}$) of less than 0.5 µm (FIG. 4). Curves 410, 420, and 430 show that the particle size of the resultant emulsions from one pass of high shear processing with 15 k, 20 k, and 25 k RPM is 0.43, 0.37, and 0.44 µm, respectively.

Example 3: High Shear Processing of Non-Pre-Emulsified Mixture

Formula C (20 wt % oil) was processed in a rotor stator high shear mixer at 25° C.-40° C. temperature for 5 minutes with a shear rate ranging from 180,000 $s^{-1}$ (15 k RPM) to 300,000 $s^{-1}$ (25 k RPM) for 5 minutes, in a recirculation mode for up to 3 passes.

Figure 5:
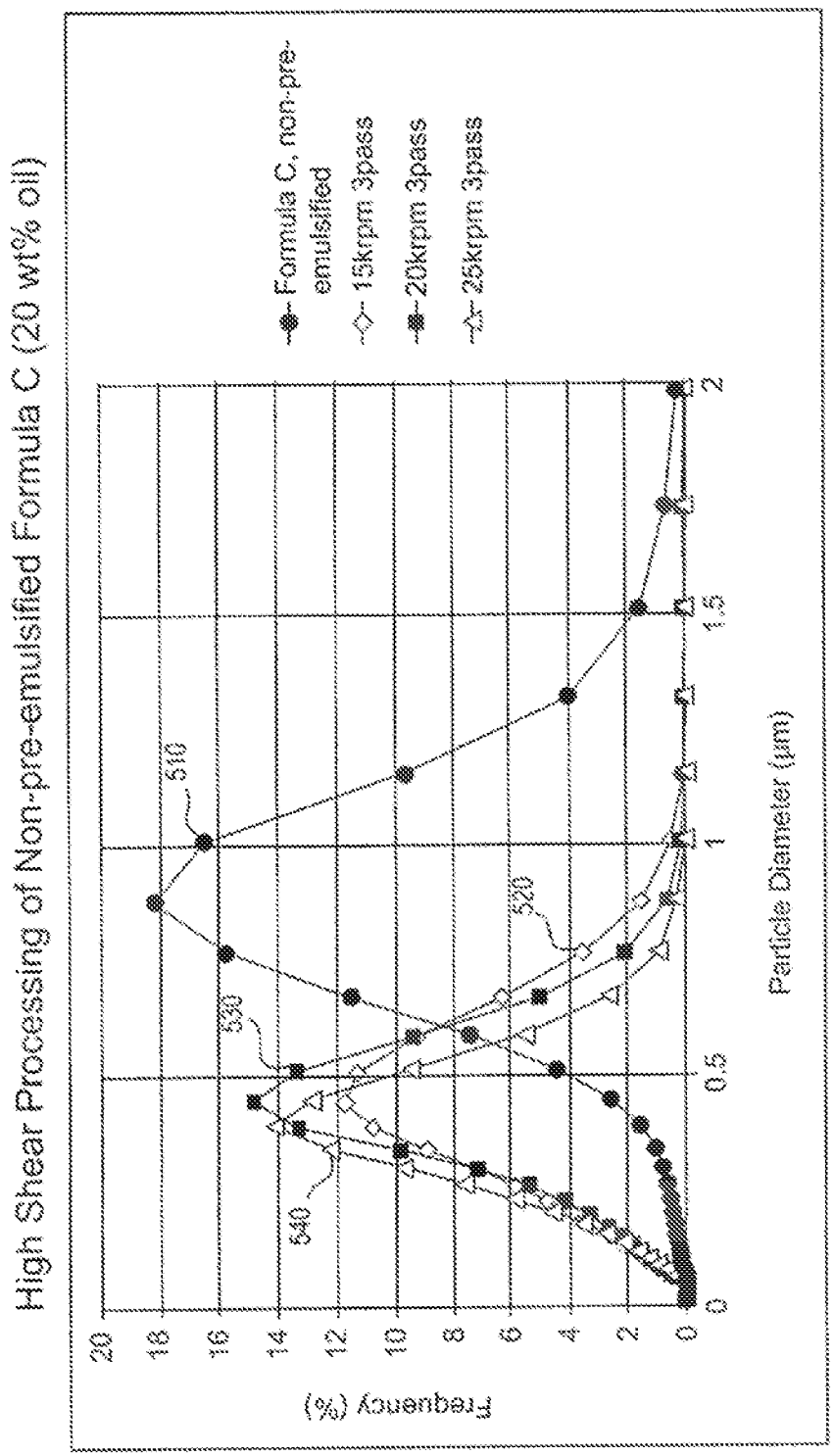
FIG. 5 shows particle sizes of the emulsions obtained from high shear processing of non-pre-emulsified formula C, and the particle size of the non-pre-emulsified formula C.

The results were shown In FIG. 5. Curves 520, 530, and 540 in FIG. 5 show that the particle size ($d_{95}$) of the resultant emulsions after three passes of high shear processing with 15 k, 20 k, and 25 k RPM is 0.69, 0.63, and 0.57 µm, respectively.

Example 4: Comparison of Pre-High Shear Mixtures and Post-High Shear Emulsions

Figure 6:
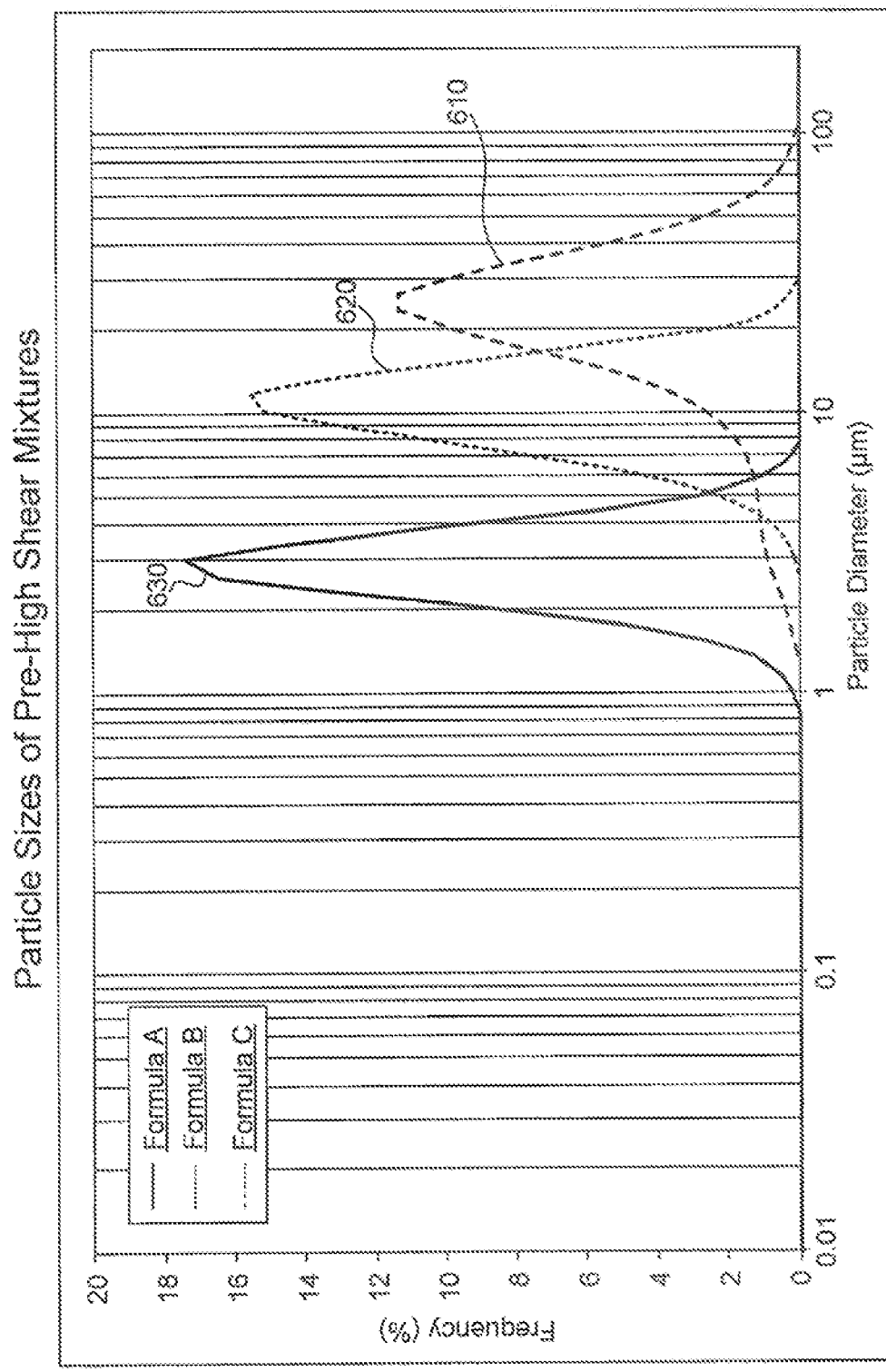
FIG. 6 shows particle sizes of the pre-high shear mixtures obtained from formulas A-C.

Formulas A-C were added in a batch mixer equipped with a central agitator and in-line rotor stator high shear mixer. Each formula was mixed with an agitator speed of 150 RPM at 20° C. and with the in-tank high shear off. The particle size of the resulting pre-high shear mixtures was measured and the results were shown in FIG. 6. Curves 610, 620, and 630 show that the particle size ($d_{95}$) of the pre-high shear mixtures derived from formulas A, B, and C is 40, 15, and 4 µm, respectively.

Figure 7:
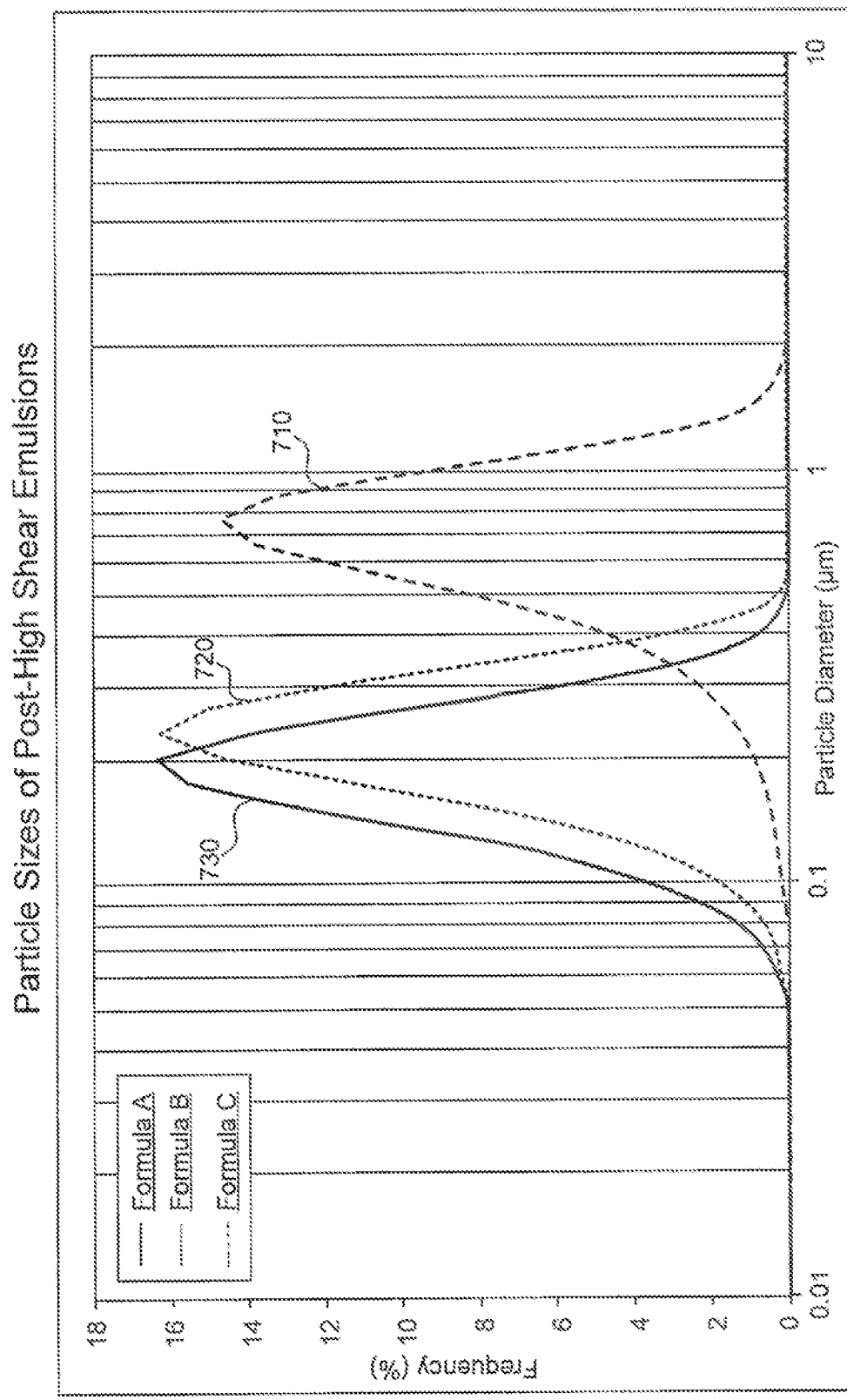
FIG. 7 shows particle sizes of the post-high shear emulsions obtained from formulas A-C.

The pre-high shear mixtures were then processed with the rotor stator high shear mixer at 2500 RPM with a shear rate of 30,000 $s^{-1}$ for 10 minutes. The particle size of the post-high shear emulsions was measured and the results were shown in FIG. 7. Curves 710, 720, and 730 indicate that the particle size ($d_{95}$) of the emulsions obtained horn formula A, B, C is 1.05, 0.32, and 0.29 µm, respectively.

Example 5: High Pressure Homogenization of Pre-Emulsified Formula A

In comparison, experiments were conducted to prepare nanoemulsions from formulas A-C by using high pressure homogenization. A pre-emulsified mixture was obtained for each of formulas A-C, as described in Example 2.

Figure 8:
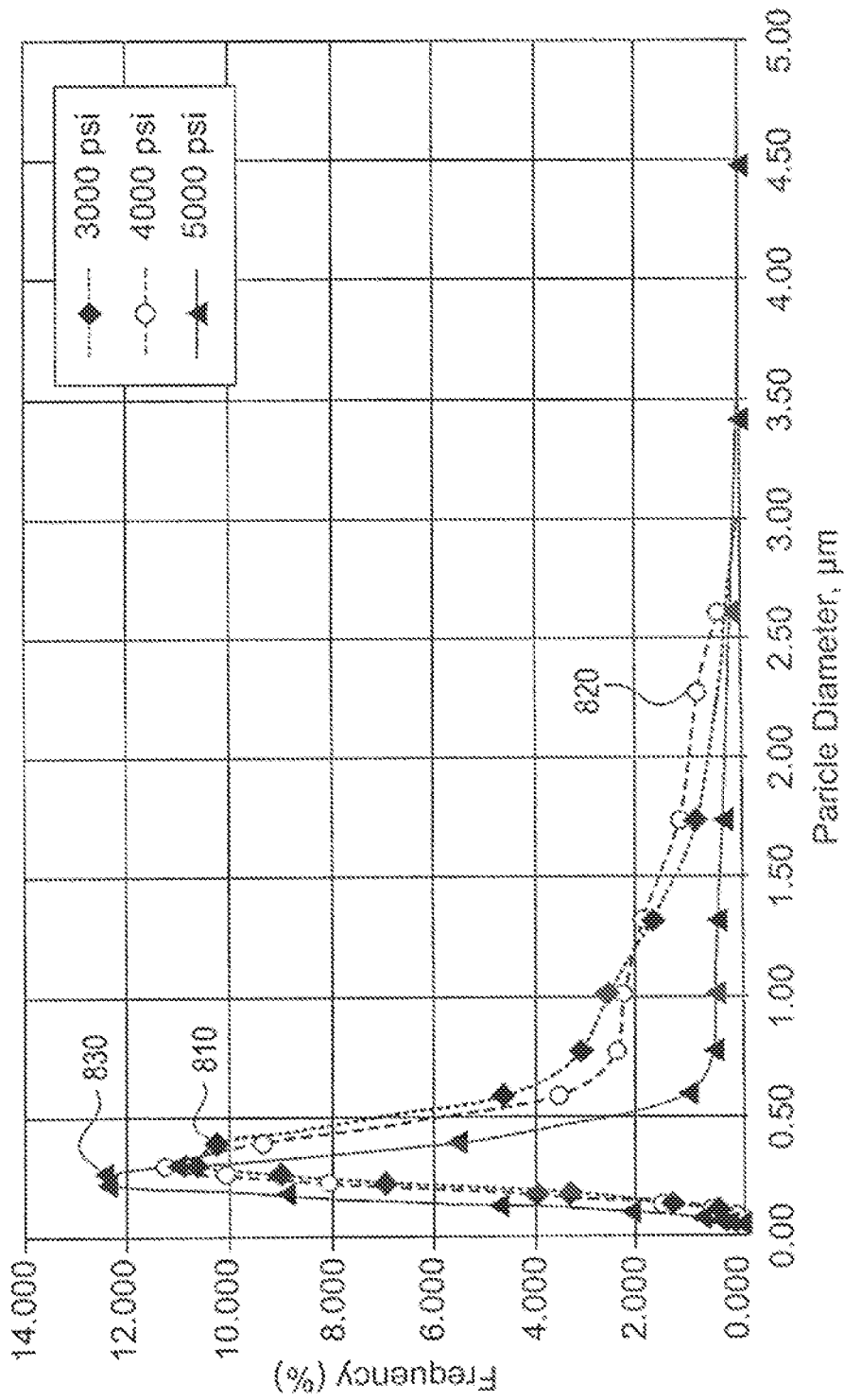
FIG. 8 shows particle sizes of the emulsions obtained from high pressure homogenization of pre-emulsified formula A after two passes under 3000, 4000, and 5000 psi.
Figure 9:
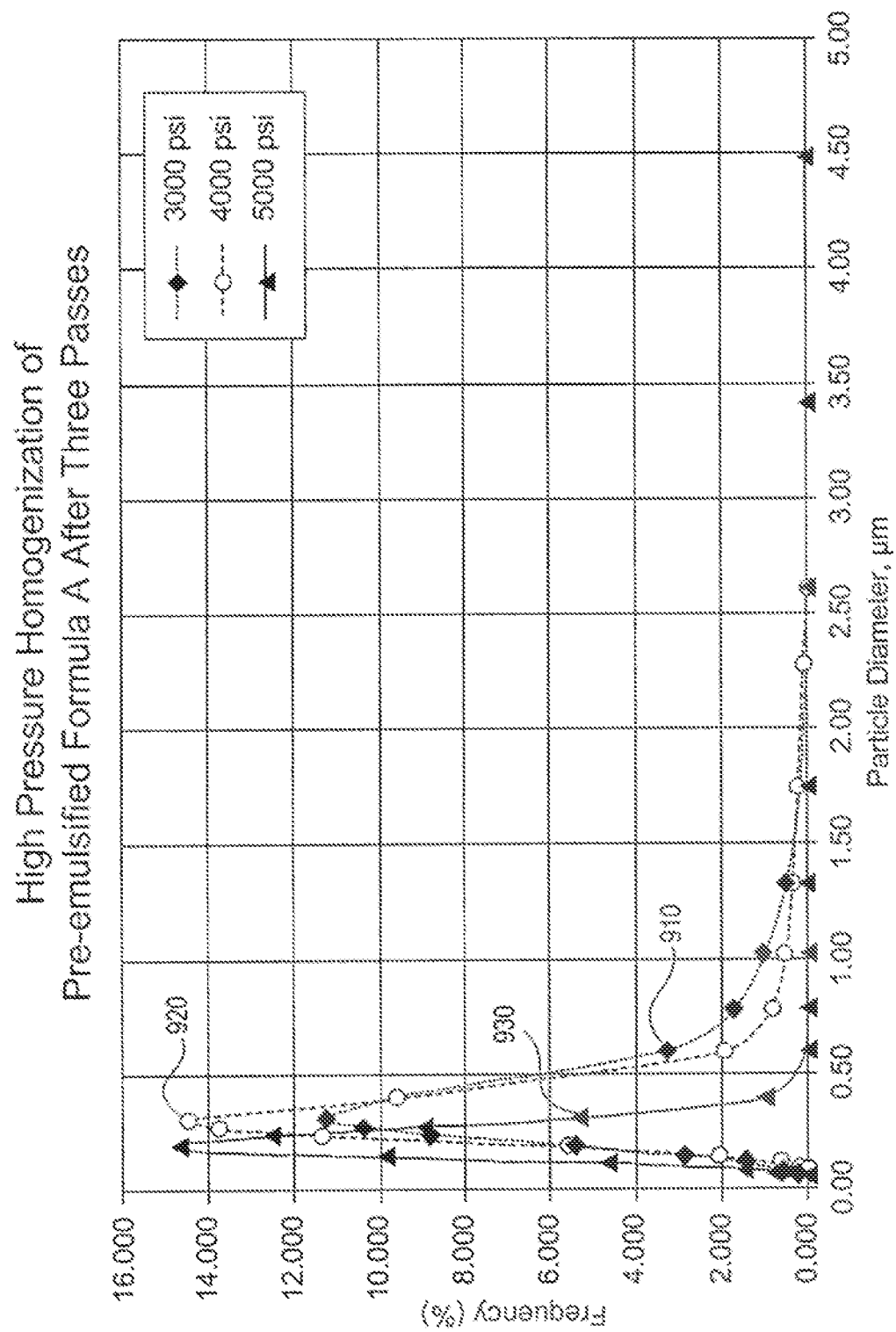
FIG. 9 shows particle sizes of the emulsions obtained from high pressure homogenization of pre-emulsified formula A after three passes under 3000, 4000, and 5000 psi.

The pre-emulsified mixture was processed through an APV high pressure homogenizer at pressures between 3000 and 5000 psi for 1, 2, and 3 passes. Curve 830 in FIG. 8 shows that formula A (10 wt % oil) provided nanoemulsions with a particle size ($d_{95}$) of less than 1 µm after two passes of homogenization under 5000 psi. Curves 910, 920, and 930 in FIG. 9 show that formula A provided nanoemulsions with a particle size ($d_{95}$) of less than 1 µm under 3000, 4000, and 5000 psi after three passes of homogenization.

Example 6: High Pressure Homogenization of Pre-Emulsified Formula B

The pre-emulsified mixture of formula B (16 wt % oil) was processed through an APV high pressure homogenizer at pressures between 3000 and 5000 psi for 1, 2, and 3 passes. It is difficult to process pre-emulsified formula B through the bench-scale high pressure homogenizer because of the high viscosity. The pre-emulsified mixture of formula B could not be processed in a larger scale high pressure homogenizer due to its high viscosity. The pre-emulsified mixture of formula C had an even higher viscosity, and could not be processed in bench-scale or larger scale high pressure homogenizers.

Figure 10:
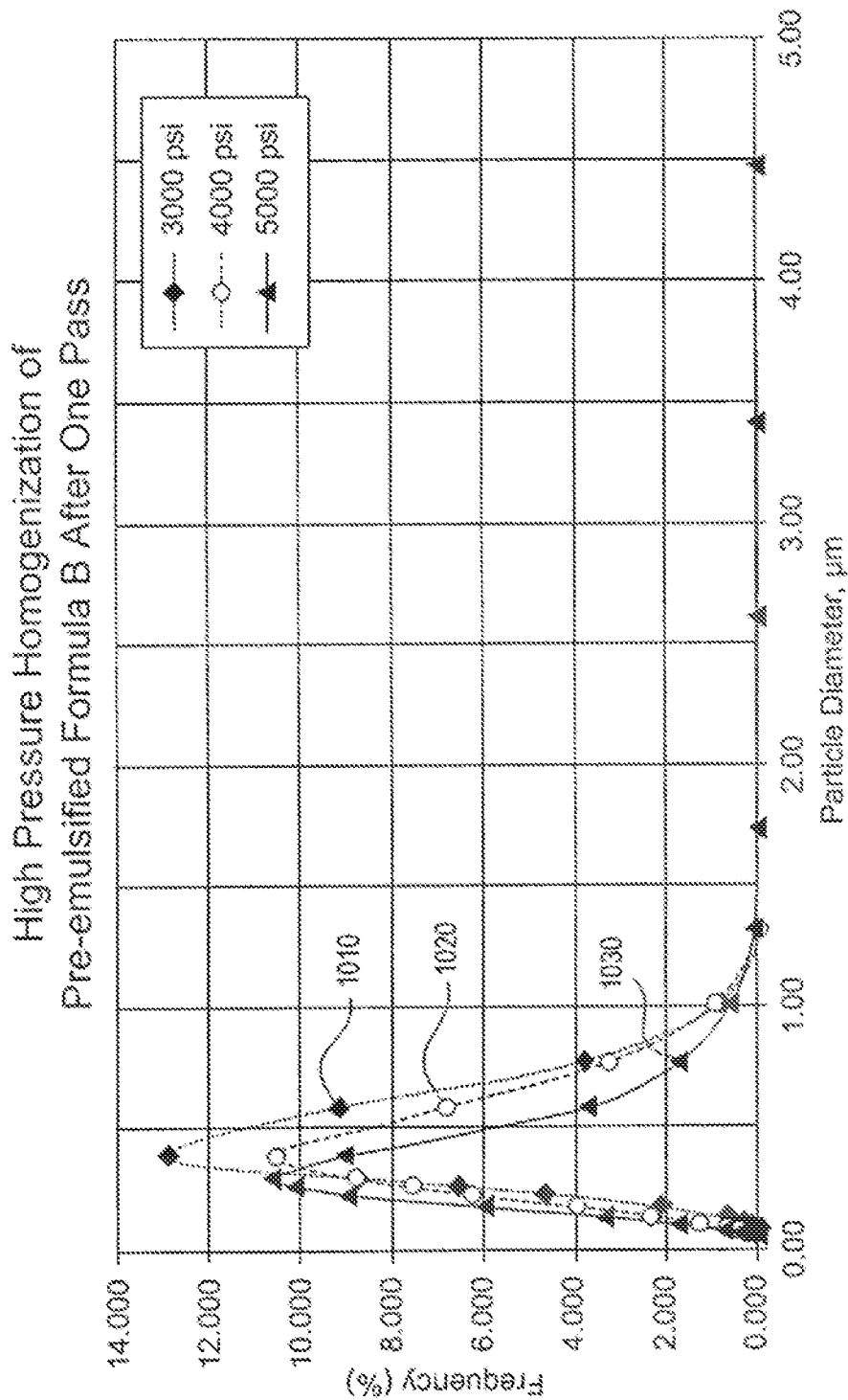
FIG. 10 shows particle sizes of the emulsions obtained from high pressure homogenization of pre-emulsified formula B after one pass under 3000, 4000, and 5000 psi.

Curves 1010, 1020, and 1030 in FIG. 10 show that the resultant emulsions had a particle size ($d_{95}$) of less than 1 μm after only one pass of homogenization under 3000 psi, 4000 psi, and 5000 psi, respectively.

Figure 11:
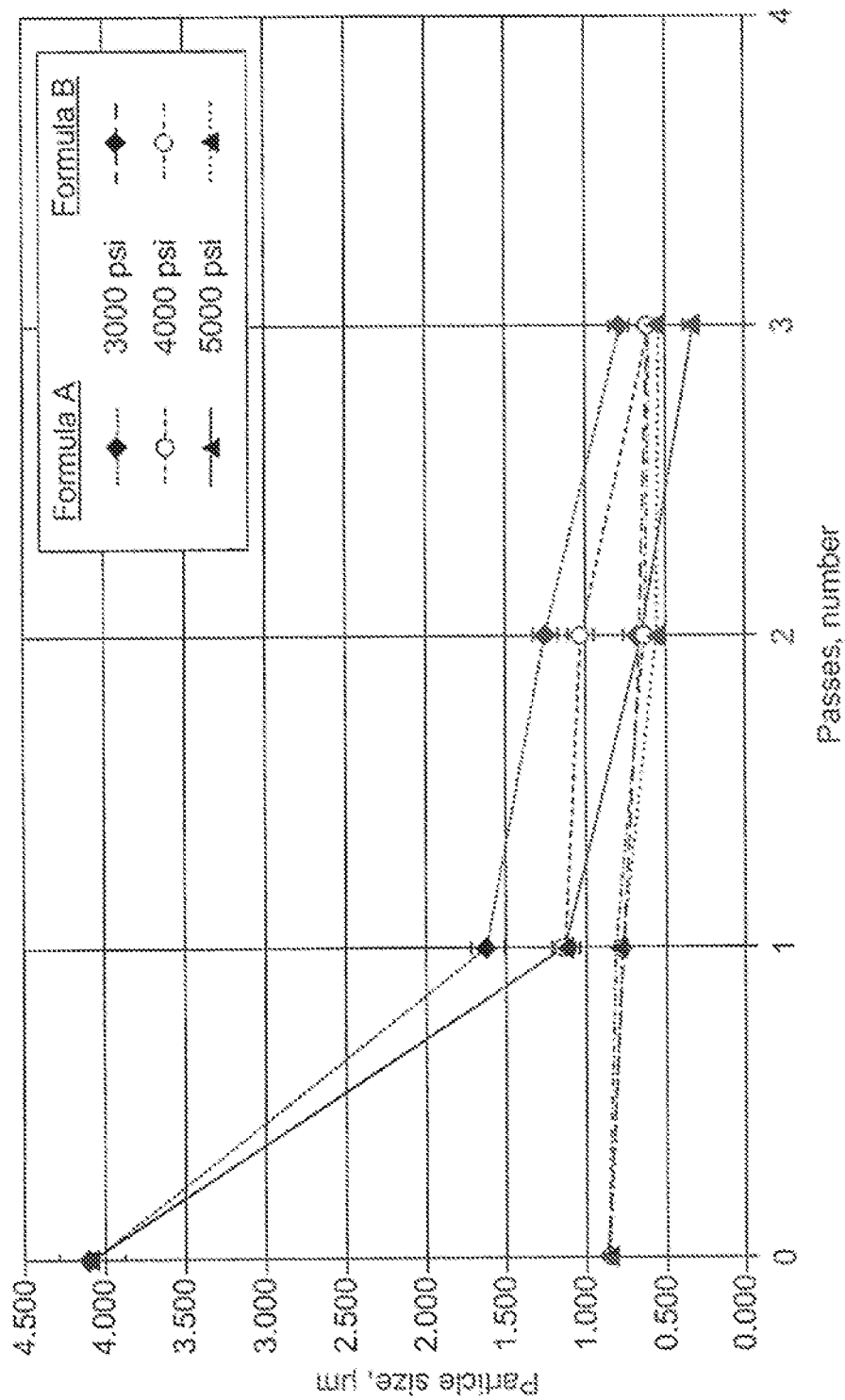
FIG. 11 shows the effects of pressure, number of passes, and emulsion concentration on the particle sizes of the emulsions obtained from high pressure homogenization of pre-emulsified formulas A and B.

The effects of the pressure and of the number of passes on the emulsion particle size are shown in FIG. 11 for pre-emulsified formulas A and B. At the number of passes of zero, the pre-emulsified formula A had a particle size ($d_{95}$) of greater than 4 μm, while the pre-emulsified formula B had a particle size ($d_{95}$) of less than 1 μm.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method for preparing a beverage nanoemulsion, comprising:
    mixing a mixture comprising from 12 wt % to 40 wt % oil, an emulsifier, and an optional preservative, with a high shear mixer at a shear rate of 150,000 $s^{-1}$ to 300,000 $s^{-1}$ to obtain the nanoemulsion, wherein the mixture has a viscosity of 2800 cp at 10 $s^{-1}$ to 50,000 cp at 10 $s^{-1}$ during at least a part of the mixing;
    wherein the nanoemulsion has a particle size of $d_{95}$ from 0.05 micron to 1 micron; and
    wherein the mixture is not processed through a high pressure homogenizer.

2. The method of claim 1, wherein the oil is a flavorless oil selected from the group consisting of medium chain triglycerides, grapeseed oil, soybean oil, palm oil, rapeseed oil, sunflower seed oil, peanut oil, cotton seed oil, olive oil, avocado oil, coconut oil, safflower oil, and combinations thereof.

3. The method of claim 1, wherein the oil is a flavor oil selected from the group consisting of citrus oil, cola oil, almond oil, grapefruit oil, cinnamon oil, lemon oil, lime oil, orange oil, peppermint oil, tangerine oil, and combinations thereof.

4. The method of claim 1, wherein the oil is a hydrophobic clouding agent selected from group consisting of sterol esters, stanol esters, and combinations thereof.

5. The method of claim 1, wherein the oil is present in an amount from 14 wt % to 28 wt %.

6. The method of claim 1, wherein the oil is present in an amount of 20 wt %.

7. The method of claim 1, wherein the emulsifier is selected from the group consisting of gum arabic, modified starch, pectin, xanthan gum, guar gum, propylene glycol alginate, and combinations thereof.

8. The method of claim 1, wherein the emulsifier is present in an amount from 1 wt % to 30 wt %.

9. The method of claim 1, wherein the emulsifier is present in an amount from 10 wt % to 30 wt %.

10. The method of claim 1, wherein the nanoemulsion has a particle size of $d_{95}$ from 0.2 micron to 0.8 micron.

11. The method of claim 1, wherein the nanoemulsion has a particle size of $d_{95}$ from 0.3 micron to 0.6 micron.

12. The method of claim 1, wherein the mixture has a viscosity of 2800 cp at 10 $s^{-1}$ to 30,000 cp at 10 $s^{-1}$ during at least a part of the mixing.

13. The method of claim 1 further comprising adding water to the nanoemulsion to obtain a diluted nanoemulsion, wherein the diluted nanoemulsion contains 6 wt % to 10 wt % of the oil, and wherein the diluted nanoemulsion has a particle size of $d_{95}$ from 0.05 micron to 1 micron.

* * * * *